(12) United States Patent
Miller et al.

(10) Patent No.: US 8,673,007 B2
(45) Date of Patent: Mar. 18, 2014

(54) IMPLANT WITH INSERTION DEVICE AND METHOD

(75) Inventors: Keith E. Miller, Germantown, TN (US); Y. Raja Rampersaud, Toronto (CA); Cristian A. Capote, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 486 days.

(21) Appl. No.: 12/763,922

(22) Filed: Apr. 20, 2010

(65) Prior Publication Data
US 2011/0257745 A1    Oct. 20, 2011

(51) Int. Cl.
*A61F 2/44* (2006.01)

(52) U.S. Cl.
USPC .................................. 623/17.12; 623/17.11

(58) Field of Classification Search
USPC ........................... 623/17.12; 606/92–94, 105
See application file for complete search history.

(56) References Cited

U.S. PATENT DOCUMENTS

| | | | |
|---|---|---|---|
| 3,875,595 A | 4/1975 | Froning | |
| 5,236,460 A | 8/1993 | Barber | |
| 6,595,952 B2 | 7/2003 | Forsberg | |
| 6,740,093 B2 | 5/2004 | Hochschuler et al. | |
| 6,887,229 B1 | 5/2005 | Kurth | |
| 7,351,238 B2 | 4/2008 | Lee et al. | |
| 7,595,082 B2 | 9/2009 | Connors, III et al. | |
| 7,628,800 B2 | 12/2009 | Sherman et al. | |
| 7,670,374 B2 | 3/2010 | Schaller | |
| 2004/0210297 A1 | 10/2004 | Lin et al. | |
| 2005/0131341 A1* | 6/2005 | McGuckin et al. | 604/43 |
| 2007/0093901 A1 | 4/2007 | Grotz et al. | |
| 2007/0161962 A1* | 7/2007 | Edie et al. | 604/257 |
| 2007/0173940 A1 | 7/2007 | Hestad et al. | |
| 2007/0250060 A1* | 10/2007 | Anderson et al. | 606/61 |
| 2008/0009828 A1 | 1/2008 | Miller et al. | |
| 2008/0021556 A1 | 1/2008 | Edie | |
| 2008/0058930 A1 | 3/2008 | Edie et al. | |
| 2008/0058931 A1 | 3/2008 | White et al. | |
| 2008/0065083 A1 | 3/2008 | Truckai et al. | |
| 2008/0097397 A1 | 4/2008 | Vrba | |
| 2008/0140109 A1 | 6/2008 | Park | |
| 2008/0147189 A1 | 6/2008 | Melkent | |
| 2008/0161933 A1 | 7/2008 | Grotz et al. | |
| 2008/0167726 A1 | 7/2008 | Melkent | |
| 2009/0270987 A1 | 10/2009 | Heinz et al. | |
| 2011/0125158 A1* | 5/2011 | Diwan et al. | 606/93 |

FOREIGN PATENT DOCUMENTS

| | | |
|---|---|---|
| DE | 20017962 U1 | 10/2000 |
| DE | 202005009478 U1 | 6/2005 |
| EP | 1212992 B1 | 11/2001 |
| EP | 1290993 A1 | 9/2002 |
| WO | 2008086274 A2 | 1/2008 |
| WO | 2008086274 A3 | 1/2008 |
| WO | 2008086276 A2 | 1/2008 |
| WO | 2008086276 A3 | 1/2008 |
| WO | 2008103466 A1 | 2/2008 |
| WO | 2008144175 A1 | 4/2008 |
| WO | 2008148210 A1 | 6/2008 |

* cited by examiner

*Primary Examiner* — Andrew Yang
*Assistant Examiner* — Olivia C Chang

(57) ABSTRACT

Embodiments of the invention include expandable medical implant systems and methods. The systems may include devices to reinforce a tube through which a fill material may be moved at least in part into expandable medical implants. In some embodiments, an implant replaces one or more of vertebral bodies, portions of vertebral bodies, discs, and portions of discs of the spine.

10 Claims, 7 Drawing Sheets

IMPLANT WITH INSERTION DEVICE AND METHOD

FIELD OF THE INVENTION

The present invention relates generally to the field of medical implants and methods for use with skeletal structures, and more particularly relates to components and methods to facilitate insertion and use of an implant.

BACKGROUND

One or more implants may be placed between vertebrae in response to various pathologies and expanded in place to better fill a space into which the one or more implants have been placed. An implant may replace all or a part of one or more vertebral discs or vertebrae. For example, implants to replace or supplement all or a part of a single spinal disc may be referred to as disc replacement devices, spinal arthroplasty devices, or interbody fusion devices. By way of further example, one or more of the vertebrae may become damaged as a result of tumor growth, or may become damaged by a traumatic or other event. Removal, or excision, of a vertebra may be referred to as a vertebrectomy. Excision of a generally anterior portion, or vertebral body, of the vertebra may be referred to as a corpectomy. An implant may be placed between the remaining vertebrae to provide structural support for the spine as a part of a corpectomy or vertebrectomy. If only a portion of a vertebral body and adjacent discs are removed and replaced, the procedure may be called a hemi-vertebrectomy.

Many implants are known in the art for use in disc replacement, interbody fusion, spinal arthroplasty, vertebrectomy, hemi-vertebrectomy, and corpectomy procedures. One class of implants is sized to directly replace an anatomic structure, without in situ expansion. Another class of implants is inserted in a collapsed state and then expanded once properly positioned. These expandable implants may be advantageous because they allow for a smaller incision and entry path when positioning an implant. Initially small implants enabling minimal tissue disruption may be useful from any surgical approach to reduce trauma to surrounding tissues and to enhance patient recovery. Expandable implants may be expanded by transfer of a fill material into the expandable implants through a hose or tube that extends from the expandable implant to connect to a fill material source. It may be desirable for some expandable implants to include an extension or handle of a relatively small diameter that will allow for the associated expandable implant to be directed to an implantation site without insertion of a surgeon's fingers or larger diameter instruments along the insertion path. The hose or tube through which fill material may be placed can provide a convenient grasping point and handling device for an expandable implant. However, the hose or tube must be adequately rigid to safely and effectively control an attached expandable implant. Sometimes it is advantageous to employ a hose or tube that is flexible in association with an expandable implant. For example and without limitation, the material properties of a flexible hose or tube may be advantageous for managing the pressure of the fill material during placement, or a flexible hose or tube may be easier or more economical to connect to the expandable implant body or to a fill material source, or a flexible hose or tube may provide for the hose or tube to be placed along a desired curvilinear path as fill material is passed through the hose or tube, or at another time during a procedure. Therefore, it may be advantageous in some circumstances to provide a flexible hose or tube that, at some times, is adequately rigid to safely and effectively be used as a handling device in placing an attached expandable implant.

Expandable implants with similar mechanisms may also be useful in replacing long bones or portions of appendages such as the legs and arms, or a rib or other bone that is generally, though not necessarily, longer than it is wide. Examples include, but are not limited to a femur, tibia, fibula, humerus, radius, ulna, phalanges, clavicle, and any of the ribs. Use of the mechanisms described and claimed herein are equally applicable to treatment or repair of such bones or appendages.

SUMMARY

One embodiment of the invention is a system configured to stabilize spaced apart skeletal structures. The system may include an expandable medical implant configured to receive a fill material, and a tubular body having a distal end and a proximal end, the tubular body being coupled to the expandable medical implant at the distal end of the tubular body and configured to provide a conduit between a fill material source and the expandable medical implant. The system may also include a reinforcing member configured to at least supplement the bending strength of the tubular body. The reinforcing member may include a distal end that provides support along at least a portion of the tubular body and a proximal end configured to securely couple over the proximal end of the tubular body.

Another embodiment of the invention is a method of stabilizing skeletal structures. The method may include providing a device including a medical implant configured to receive a fill material. The device may also include a fill material source, a tubular body coupled to the expandable medical implant and configured to provide a conduit between the fill material source and the expandable medical implant, and a reinforcing member configured to couple with the tubular body. The reinforcing member may provide at least some increased rigidity to the tubular body beyond the rigidity of the tubular body and cover a proximal end of the tubular body. The method may include grasping the device by one or both of the tubular body and the reinforcing member, and inserting the device between skeletal structures by manipulating the device from one or both of the grasped tubular body and the reinforcing member. The method may also include removing the reinforcing member from a coupling with the tubular body wherein the reinforcing member covering the proximal end of the tubular body is removed from covering the proximal end of the tubular body, and transferring fill material through the uncovered proximal end of the tubular body and into the medical implant.

Yet another embodiment of the invention is a method of stabilizing skeletal structures. The method may include providing a device that includes an expandable medical implant configured to receive a fill material, a fill material source, and a tubular body having a distal end and a proximal end. The tubular body may be coupled to the expandable medical implant at the distal end of the tubular body and configured to provide a conduit between the fill material source and the expandable medical implant. The device may also include a reinforcing member configured to at least supplement the bending strength of the tubular body, wherein the reinforcing member includes a distal end that provides support along at least a portion of the tubular body and a proximal end configured to couple over the proximal end of the tubular body. The method may include grasping the device by one or both of the tubular body and the reinforcing member, and inserting the device between skeletal structures by manipulating the device by one or both of the tubular body and the reinforcing member. The method may also include transferring fill material from the fill material source, through the proximal end of the tubular body, and into the medical implant.

DETAILED DESCRIPTION

Figure 7:
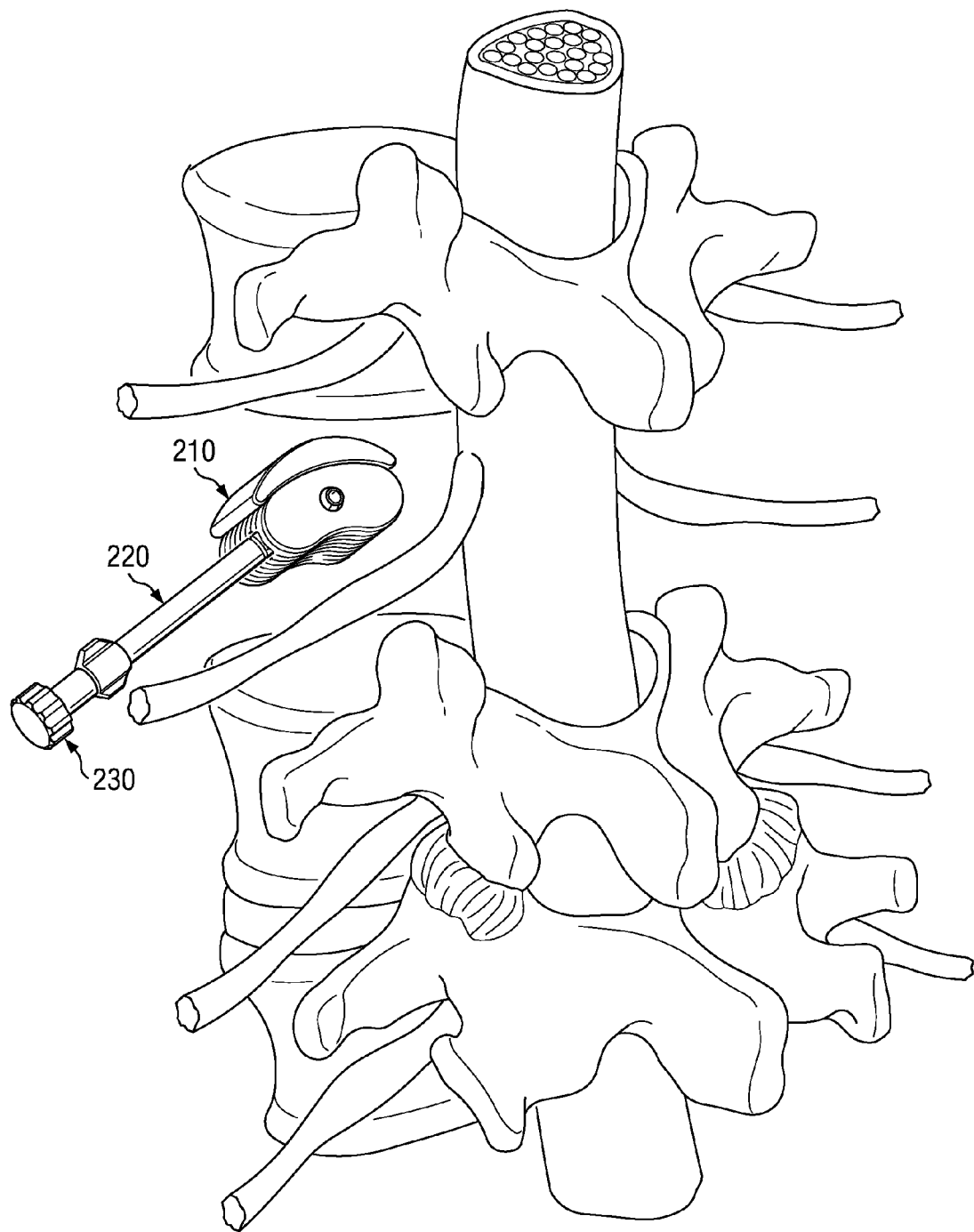
FIG. 7 is a perspective view of an embodiment of a system configured to stabilize spaced apart skeletal structures being inserted between skeletal structures.
Figure 8:
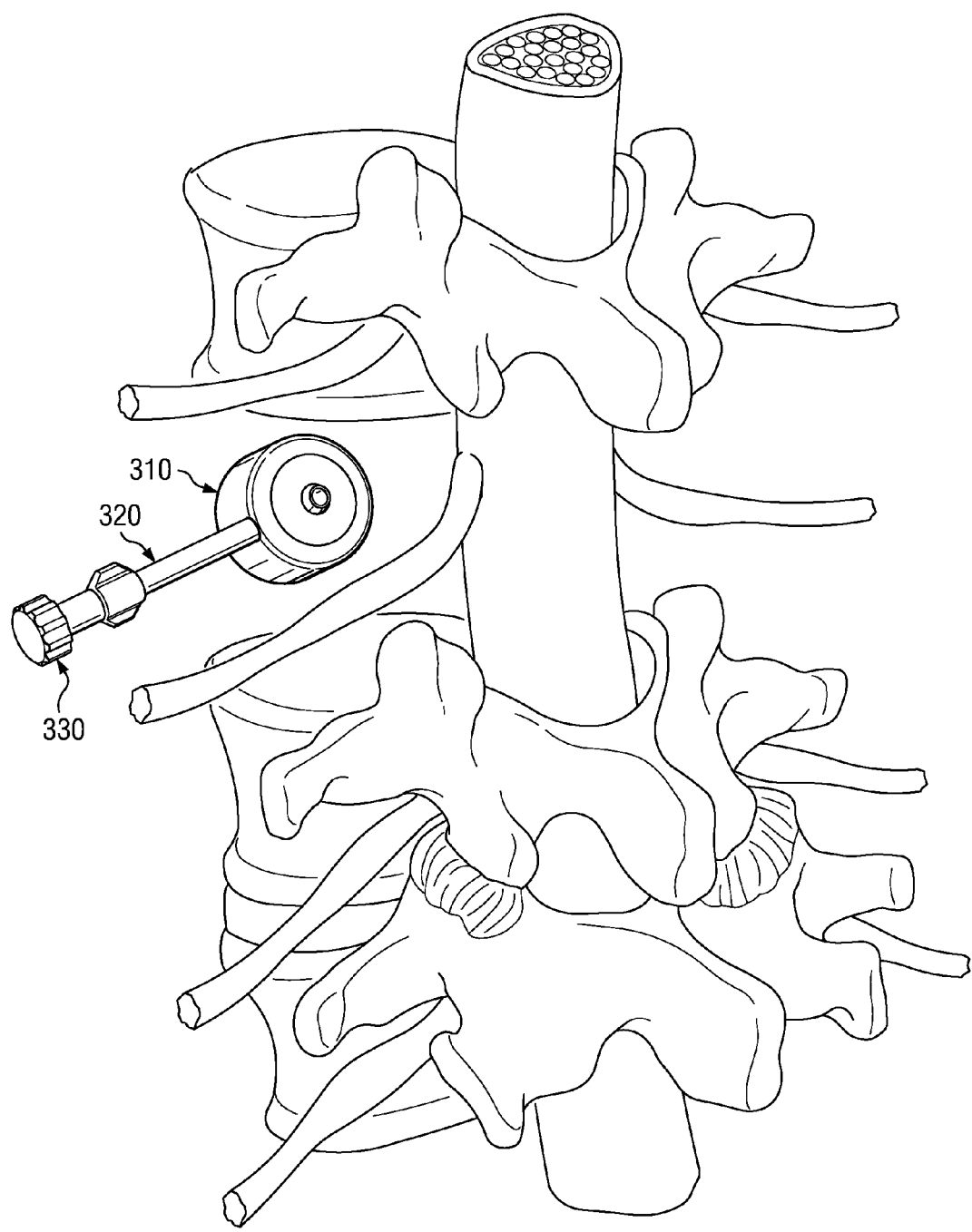
FIG. 8 is a perspective view of an embodiment of a system configured to stabilize spaced apart skeletal structures being inserted between skeletal structures.

An embodiment of a system 1 configured to stabilize spaced apart skeletal structures is illustrated in FIGS. 1-6C, in whole and in its component parts. Two additional embodiments of systems configured to stabilize space apart skeletal structures are illustrated in FIGS. 7 and 8 respectively. The system 1 that is shown includes an expandable medical implant 10 configured to receive a fill material 100 (FIG. 5), a tubular body 20 coupled to the expandable medical implant 10, and a reinforcing member 30 configured to at least supplement the bending strength of the tubular body 20. The expandable medical implant 10 shown in the illustrated embodiment is a vertebral body replacement device. The illustrated expandable medical implant 10 includes a membrane 15 configured to expand at least laterally when filled with the fill material 100. In various embodiments, an expandable medical implant may be used in association with corpectomy, vertebrectomy, and hemi-vertebrectomy procedures. Similarly, expandable medical implants with some common features may be used at least in part in an interbody space as spinal joint arthroplasty devices, vertebral disc replacement or supplementation devices, and fusion devices. The expandable medical implant 10 may be embodied in any of the variations of expandable medical implants presented in U.S. patent application Ser. No. 12/763,883, entitled, "EXPANDABLE MEDICAL DEVICE AND METHOD," filed on the same day herewith, and which is hereby incorporated by reference herein.

Figure 1:
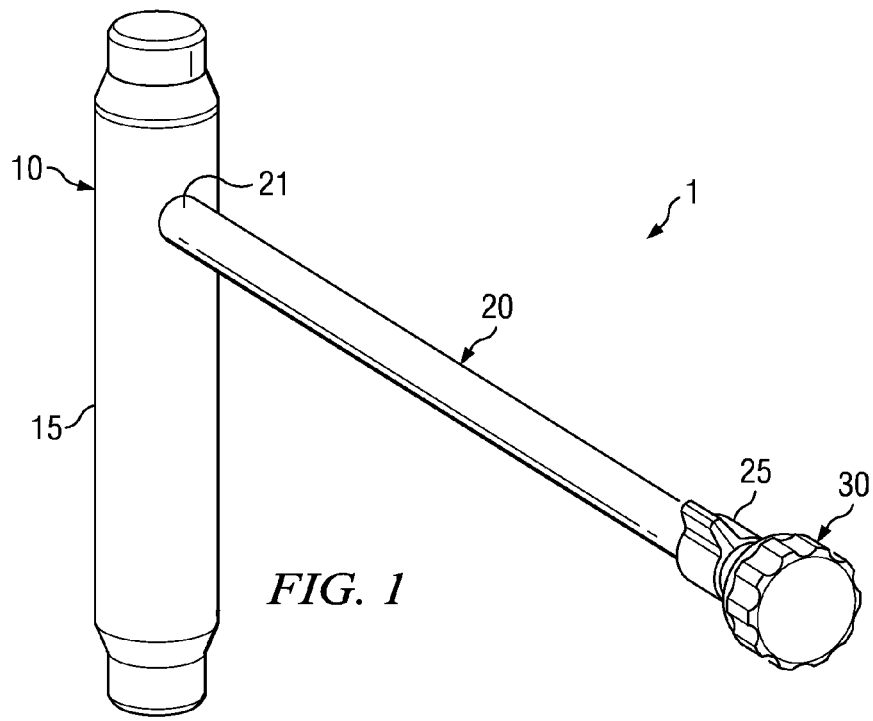
FIG. 1 is perspective view of an embodiment of a system configured to stabilize spaced apart skeletal structures.
Figure 2:
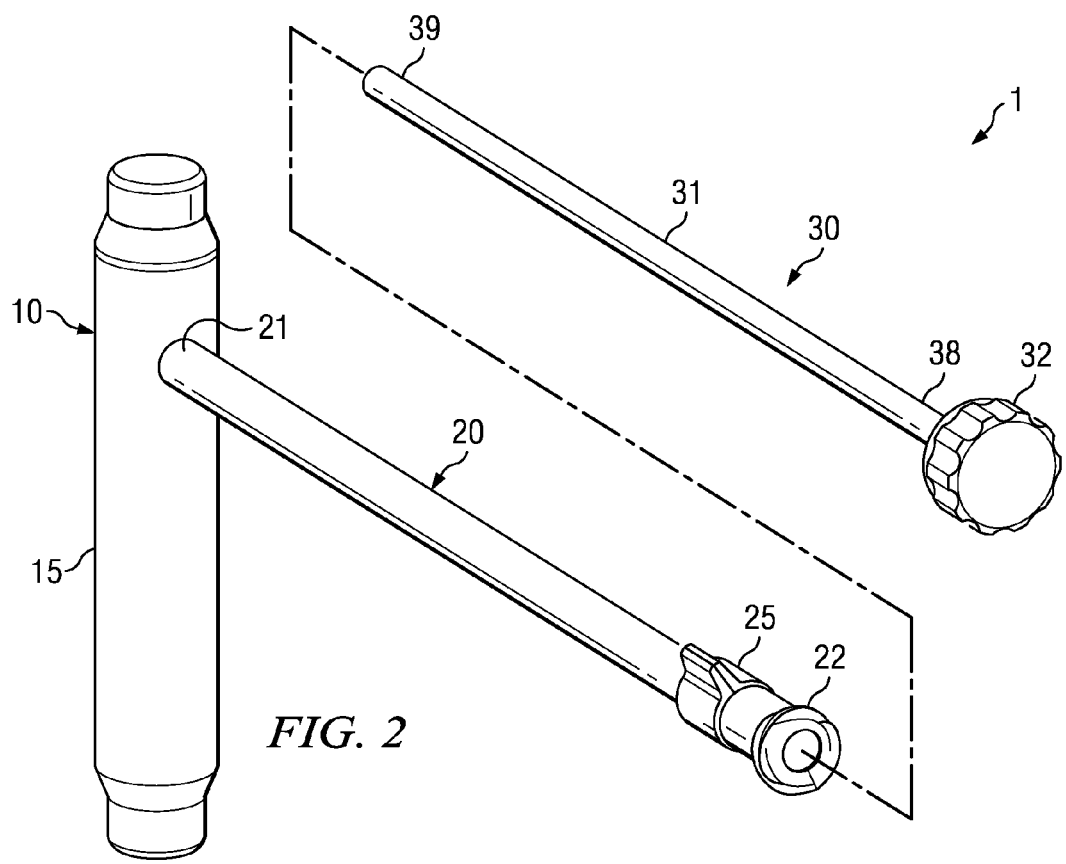
FIG. 2 is a partially exploded perspective view of the embodiment of FIG. 1.
Figure 5:
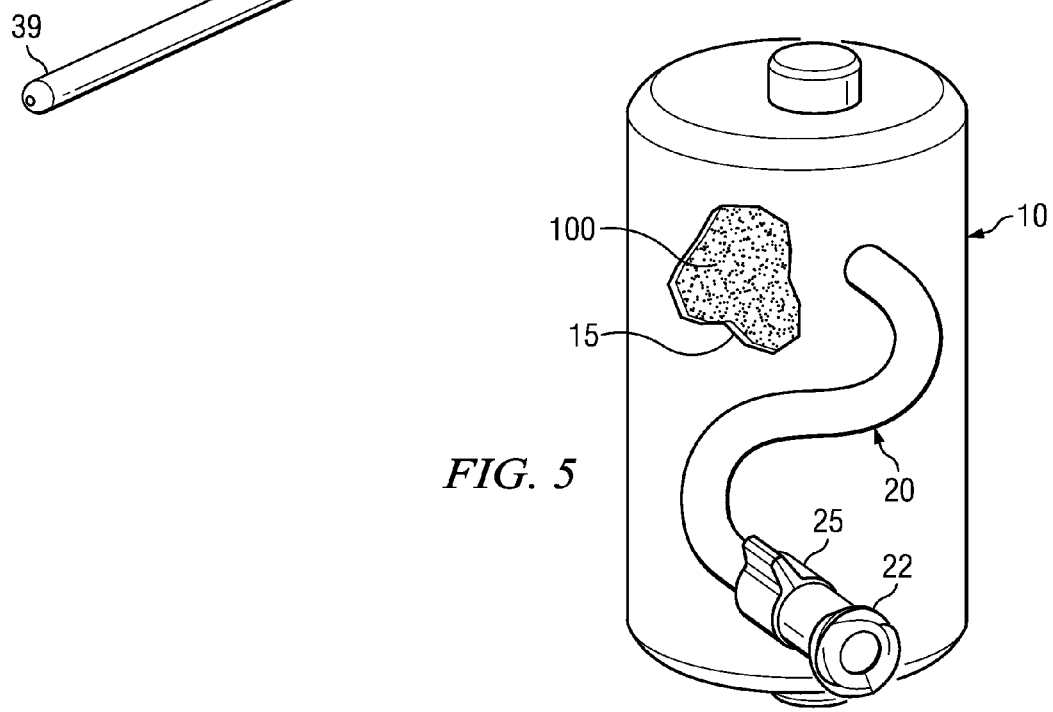
FIG. 5 a perspective view of the embodiment of FIG. 1 in an at least partially expanded state with a reinforcing member removed.

The tubular body 20 shown in FIGS. 1-3 and 5-6C has a distal end 21 (FIGS. 1 and 2) and a proximal end 22 (FIGS. 2 and 5). The tubular body 20 shown has a generally round cross-sectional shape. However, in other embodiments, a tubular body may be of any effective shape or combination of shapes. By way of non-limiting example, the cross-sectional shape of a tubular body may be oval, rectangular, square, triangular, or any other polygonal shape, irregular along its length, or may include one or more of multiple shapes and multiple cannulated structures. The tubular body 20 is shown coupled to the expandable medical implant 10 at the distal end 21 of the tubular body 20. This coupling may be accomplished with an adhesive, by welding, by forming the tubular body with the expandable medical implant 10, or by any other effective mechanism or material. The tubular body 20 may be connected directly to the membrane 15 or may connect to a component within the expandable medical implant 10. If the tubular body 20 penetrates the membrane 15, the membrane 15 may include a seal configured to move along the tubular body 20 as the membrane 15 is filled. In some embodiments, the membrane 15 may include or is attached to a sleeve that extends along a length of the tubular body 20 such that the sleeve is rolled away from the center of the expandable medical implant 10, but maintains a seal along the tubular body 20, as the membrane 15 is filled. In the illustrated embodiment, the tubular body 20 includes a luer lock connection component 25 for securely connecting the tubular body 20 to a fill material source. The illustrated tubular body 20 therefore provides a conduit between a fill material source and the expandable medical implant 10. Any other effective fluid connection device or method may be used to connect a fill material source to the tubular body 20, and consequently, the expandable medical implant 10.

The membrane 15 of some embodiments is configured to be placed between first and second vertebrae V1, V2 (FIGS. 6A-6C) such that an upper surface of the membrane 15 contacts the first vertebra V1, and an opposite lower surface of the membrane 15 contacts the second vertebra V2 to provide support between the first and second vertebrae V1, V2. Lateral expansion of the membrane 15 is also accomplished in some embodiments. For example, in FIGS. 5 and 6C, anterior, posterior, and medial-lateral expansion, and intervening radial expansions, are illustrated. The membrane 15 may be constructed, in whole or in part, of a non-permeable material. The membrane 15 may include compliant or non-compliant balloon materials such as those commonly used to manufacture coronary and Kyphoplasty medical devices. Such materials may include, but are not limited to, mylar, rubber, polyurethane, vinyl, latex, polyethylenes, ionomer, and polyethylene terephthalate (PET), as well as less flexible materials such as Kevlar®, PEBAX®, stainless steel, titanium, nickel-titanium alloys, and other metals and alloys and/or ceramics. A compliant membrane may include reinforcing to limit one or both of the size and shape of the membrane to a clinically advantageous extent. A non-compliant membrane may expand more elastically to more completely fill an irregular opening, depending on the amount of material introduced into the membrane.

The membrane 15 may be constructed, in whole or in part, of a permeable material, which allows a certain amount of a fill material to pass through the membrane 15. All or a portion of the membrane 15 may be made permeable by fabricating a material, including but not limited to, the membrane materials listed above, into a fabric, weave, mesh, composite, bonded fiber assembly, or any other manufacture known to those skilled in the art. For example, all or part of the upper surface and the opposite lower surface of the membrane 15 may be constructed of a permeable material to allow a fill material to move through the membrane 15 and to come into contact with vertebrae V1, V2.

The tubular body 20 of some embodiments is a flexible construct. The tubular body 20 illustrated, or any other effective tubular body embodiment, may be made from a flexible material or may be made from a combination of materials assembled such that the combination is flexible. Materials may be, for example and without limitation, combined into a fabric, weave, mesh, composite, bonded fiber assembly, or any other manufacture known to those skilled in the art. The tubular body may be made from materials such as, but not limited to, mylar, rubber, polyurethane, vinyl, latex, low density polyethylene, other polyethylenes, ionomer, polyethylene terephthalate (PET), polypropylene, nylon, polystyrene, Hytrel®, Kraton® (TPE), polyolefins, and PEBAX®.

The term "flexible" as applied to a tubular body, such as the tubular body 20, means a tubular body acting alone that will not support the weight or associated insertion force of a connected expandable medical implant in a direction transverse to a longitudinal axis of the tubular body without significant deformation. Significant deformation may be, for example, angular deformation of the tubular body of over about five degrees. Such deformation may be detrimental to controlled manipulation and insertion of an expandable medical implant where the device is being held at least in part by an attached tubular body.

The reinforcing member 30 illustrated in FIGS. 1-4 and 6A-6B is configured to at least supplement the bending strength of the tubular body 20 by providing a rod 31 that is configured to fit within an inside diameter of the tubular body 20. The rod 31 may be made from any generally rigid material acceptable for at least temporary insertion into a patient. Non-limiting examples include metal, plastic, and composite materials of various types. Embodiments of a rod may include one or both of solid and hollow portions. An acceptable rod 31 may include any material and shape with sufficient rigidity to supplement the bending strength of the tubular body 20 to reduce the flexibility of the construct such that the expandable medical implant 10 may be manipulated and inserted safely between skeletal structures.

Figure 3:
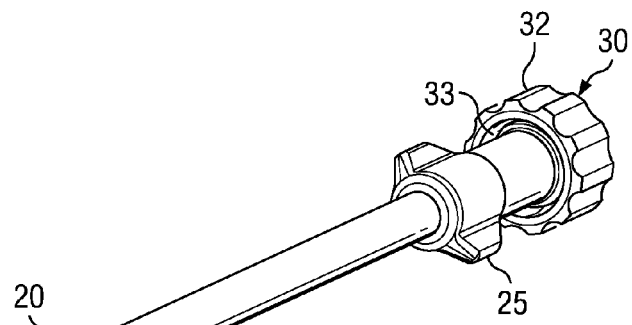
FIG. 3 is a perspective view of the embodiment of FIG. 1 with a portion of the system cut away to better illustrate features of the system.
Figure 4:
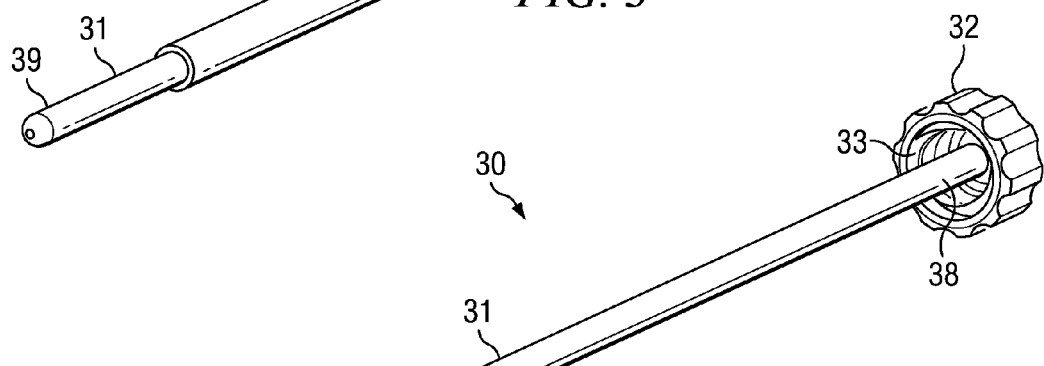
FIG. 4 is a perspective view of a reinforcing member of the embodiment of FIG. 1.

The illustrated reinforcing member 30 includes the rod 31 along with a knob 32 that is coupled with the rod 31 near a proximal end 38 of the reinforcing member 30. As shown in FIGS. 3 and 4, the knob 32 includes knob threads 33 configured at least to engage with the luer lock connection component 25 (FIGS. 1, 2, 3, and 5) that is part of the tubular body 20. The proximal end 38 of the reinforcing member 30 may be securely coupled with the proximal end 22 of the tubular body 20 by engagement of the knob threads 33 with the luer lock connection component 25 of the tubular body 20. A secure coupling is achieved by engagement between such mechanisms as the knob threads 33 and the luer lock connection component 25. However, a tubular body that merely resided in or is laid alongside a reinforcing member would not represent devices configured to "securely couple" to one another, as used herein. Other mechanisms that may provide a secure coupling include one or more clamps, pins, threaded fasteners, interference fit mechanisms, and any other effective mechanisms. The knob 32 securely couples over the proximal end 22 of the tubular body 20 in the illustrated embodiment of FIGS. 1-3 and 6A-6C. A mechanism that allows a tubular body to extend beyond an end of the reinforcing member to which the tubular body is coupled may not be "over" a proximal end of an associated tubular body. The reinforcing member 30, and specifically the knob 32, fully covers the proximal end 22 of the tubular body 20 in the illustrated embodiment and is over the proximal end 22. In other embodiments, a reinforcing member may provide only a partial covering of a proximal end of a tubular body.

Support may be provided to the tubular body 20 by the rod 31 at and near a distal end 39 of the rod 31, and along the rod 31 of the reinforcing member 30. The support provided to the tubular body 20 may be supplementation of one or more of the rigidity, bending strength, shear strength, torsional strength, and axial strength of the tubular body 20. A rod, such as the rod 31 illustrated, is round in cross-section, but may be of any effective cross-sectional shape, including but not limited to, oval, rectangular, square, triangular, or any other polygonal shape, irregular along its length, or may include one or more of these shapes combined. A rod may have a cross-sectional shape similar to or complementary with the cross-sectional shape of a cannula in a tubular body of the same system.

In some embodiments, a reinforcing member may be or include a tube configured to fit over an outside diameter of a tubular body, such as the tubular body 20. Such reinforcing member embodiments provide support to the tubular body 20 by contact with outer portions of the tubular body 20 along at least a portion of the tubular body 20. Such reinforcing member embodiments may be removed from over the proximal end 22 of a tubular body 20 to allow for introduction of a fill material, or in yet another embodiment, may include an opening or a port that may be closed or opened to provide a location for the introduction of a fill material.

In some embodiments, a reinforcing member may be a cannulated rod configured to fit within an inside diameter of a tubular body, such as the tubular body 20. Such reinforcing member embodiments provide support to the tubular body 20 in a way similar to the reinforcing member 30. Such reinforcing member embodiments may include a fitting for connection to a fill material source that provides a pathway through a cannula in the reinforcing member, and consequently through the tubular body 20 and into the expandable medical implant 10.

The fill material 100 may be introduced into the expandable medical implant 10 as a fluid, and then harden or cure in the implant. In some embodiments, a non-hardenable and non-curing fluid may be used to fill the implant or one or some portion of the implant. The fill material 100 may be a paste, gel, liquid, suspension, granular mixture, or similar substance. Non-limiting examples of fill materials 100 include bone cement, paste, morselized allograft, autograft, or xenograft bone, ceramics, or various polymers. An example bone cement is polymethylmethacrylate (PMMA), which may be made from methylmethacrylate, polymethylmethacrylate, esters of methacrylic acid, or copolymers containing polymethylmethacrylate and polystyrene. Additional non-limiting examples of the fill material 100 include semi-rigid flowable or hardenable material such as silicone or various types of urethane materials. It should further be understood that other types of fill materials 100 which are not necessarily hardenable or curable may be used in association with the present invention. For example, the fill material 100 may comprise beads or small particles or grains of material, some of which may, in aggregate, achieve a harder consistency as a result of interlocking or compaction. In some embodiments, the fill material 100 may also include any bone growth promoting substance. A fill material source may transfer or move the fill material 100 into the expandable medical implant 10 by pressure or force generated by a syringe, injector, multi-stage injector, central pressurization reservoir, rod pusher, or any effective system or device. The fill material may be fluid that is introduced only to expand the implant, or may be a final fill material. When the fluid introduced to expand the implant is not, or is not a component of, the final fill material, the fluid may be removed from the implant and be replaced in whole or in part by the fill material. The introduced fluid may also be a part of a multi-part fill material.

Embodiments of the system in whole or in part may be constructed of biocompatible materials of various types. Examples of various system materials include, but are not limited to, non-reinforced polymers, carbon-reinforced polymer composites, PEEK and PEEK composites, low density polyethylene, shape-memory alloys, titanium, titanium alloys, cobalt chrome alloys, stainless steel, ceramics and combinations thereof. If a trial instrument or implant is made from radiolucent material, radiographic markers can be located on the trial instrument or implant to provide the ability to monitor and determine radiographically or fluoroscopically the location of the body in the spinal space. In some embodiments, the implant or individual components of the implant may be constructed of solid sections of bone or other tissues. Tissue materials include, but are not limited to, synthetic or natural autograft, allograft or xenograft, and may be resorbable or non-resorbable in nature. Examples of other tissue materials include, but are not limited to, hard tissues, connective tissues, demineralized bone matrix and combinations thereof.

Some embodiments of the invention may be applied in the lumbar spinal region. Some embodiments may be applied to the cervical or thoracic spine or between other skeletal structures.

Some embodiments may also include supplemental fixation devices in addition to or as part of the expandable medical implant for further stabilizing the anatomy. For example, and without limitation, rod and screw fixation systems, anterior, posterior, or lateral plating systems, facet stabilization systems, spinal process stabilization systems, and any devices that supplement stabilization may be used as a part of or in combination with the expandable medical implant. Embodiments of the invention may be useful in at least some spinal fusion procedures where a spinal disc is replaced without replacing a vertebral body.

An alternate embodiment of a system configured to stabilize spaced apart skeletal structures is illustrated in FIG. 7. An expandable medical implant 210 configured to receive fill material is shown. The expandable medical implant 210 may also be embodied in any of the variations of expandable medical implants presented in U.S. patent application Ser. No. 12/424,941, entitled, "MINIMALLY INVASIVE EXPANDABLE VERTEBRAL IMPLANT AND METHOD" and filed on Apr. 16, 2009, which is hereby incorporated by reference in its entirety herein. A tubular body 220 is shown coupled to the expandable medical implant 210 that is configured to provide a conduit between a fill material source and the expandable medical implant 210. The tubular body 220 may be a flexible construct in some embodiments. A reinforcing member 230 is illustrated providing supplemental bending strength to the tubular body 220. All of the features, mechanisms, components, and uses disclosed with regard to other expandable medical implants, reinforcing members, and tubular bodies herein are equally applicable to variations to the tubular body 220 and the reinforcing member 230.

Another alternate embodiment of a system configured to stabilize spaced apart skeletal structures is illustrated in FIG. 8. An expandable medical implant 310 configured to receive fill material is shown. The expandable medical implant 310 may also be embodied in any of the variations of expandable medical implants presented in U.S. patent application Ser. No. 12/424,880, entitled, "MINIMALLY INVASIVE EXPANDABLE CONTAINED VERTEBRAL IMPLANT AND METHOD" and filed on Apr. 16, 2009, which is hereby incorporated by reference in its entirety herein. A tubular body 320 is shown coupled to the expandable medical implant 310 that is configured to provide a conduit between a fill material source and the expandable medical implant 310. The tubular body 320 may be a flexible construct in some embodiments. A reinforcing member 330 is illustrated providing supplemental bending strength to the tubular body 320. All of the features, mechanisms, components, and uses disclosed with regard to other expandable medical implants, reinforcing members, and tubular bodies herein are equally applicable to variations to the tubular body 320 and the reinforcing member 330.

An embodiment of the invention is a method of stabilizing spaced apart skeletal structures. Method embodiments may be accomplished with a device including a medical implant configured to receive a fill material, such as the expandable medical implant 10, and a fill material source, such as the fill material sources disclosed herein and including a supply tube 120 with supply luer lock 125, as illustrated in FIG. 6C. A tubular body, such as the tubular body 20, coupled to the expandable medical implant 10 and configured to provide a conduit between the fill material source and the expandable medical implant 10, and a reinforcing member 30 configured to couple with the tubular body 20, providing at least some increased rigidity to the tubular body 20 beyond the rigidity of the tubular body 20 and cover a proximal end 22 (FIGS. 2 and 5) of the tubular body, may also be provided. In some embodiments, the reinforcing member 30 may be provided pre-installed in the tubular body 20. However, in some embodiments, the reinforcing member 30 may need to be moved into the tubular body 20 before implanting the device. In the illustrated embodiment, the reinforcing member 30 is engaged with the tubular body, at least in part, by the act of engaging the knob threads 33 of the reinforcing member 30 with the luer lock connection component 25. Threads may be included on one or both of the tubular body 20 and the reinforcing member 30 in various embodiments, or coupling may be accomplished with other effective mechanisms, at least as disclosed herein.

Figure 6A:
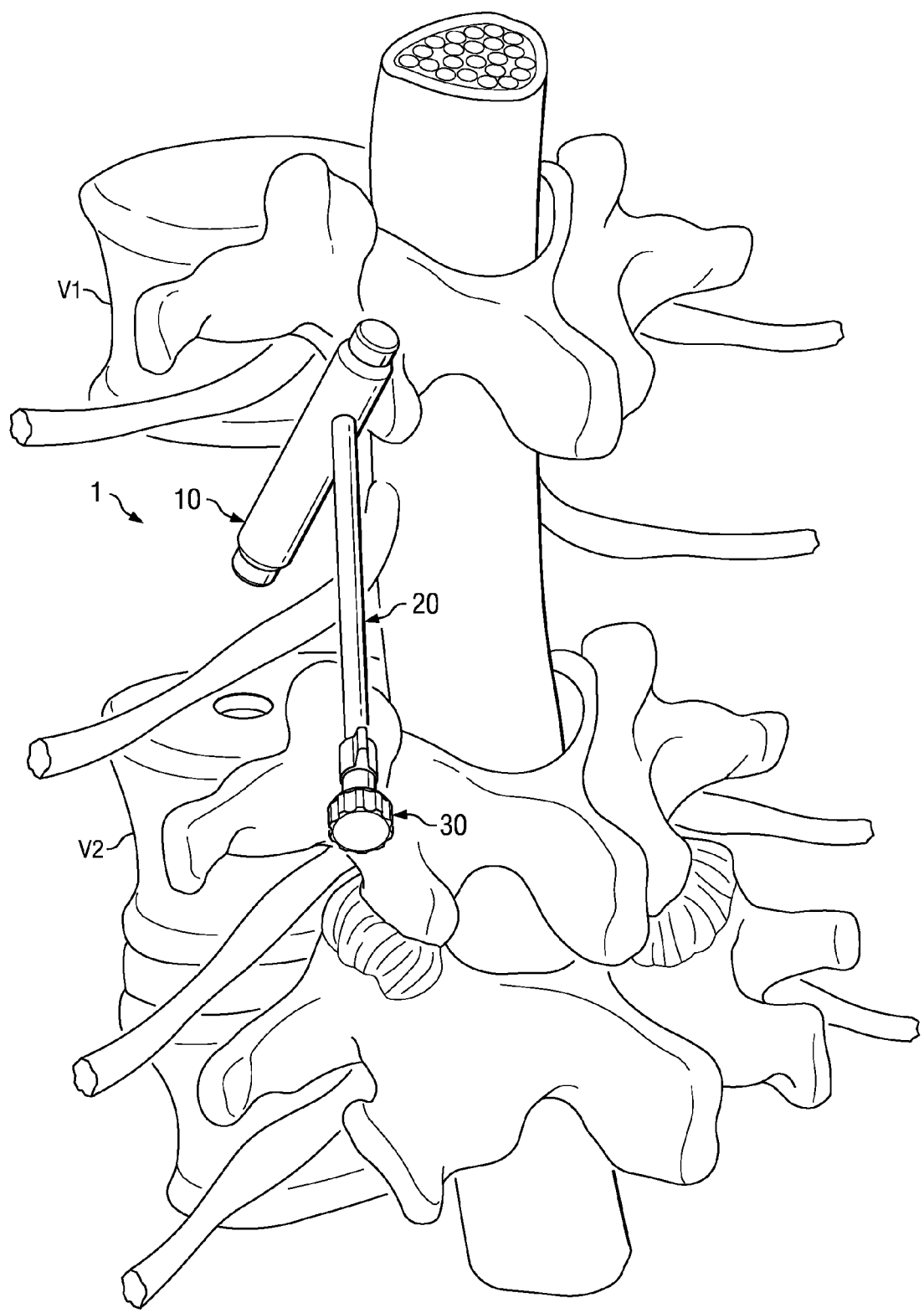
FIG. 6A is a perspective view of the embodiment of FIG. 1 being inserted between skeletal structures.

Method embodiments may also include grasping the device by one or both of the tubular body 20 and the reinforcing member 30 shown in FIG. 6A. The device may further be inserted between skeletal structures, such as skeletal structures first vertebra V1 and second vertebra V2 illustrated in FIGS. 6A-6C, by manipulating the device from one or both of the grasped tubular body 20 and the reinforcing member 30. Some embodiments include removing the reinforcing member 30 from a coupling with the tubular body 20 wherein the reinforcing member 30 covering the proximal end 22 of the tubular body 20 is removed from covering the proximal end 22 of the tubular body 20, as is illustrated in the exploded view of FIG. 2.

Method embodiments may include transferring fill material 100 through the uncovered proximal end 22 of the tubular body 20 and into the expandable medical implant 10. The tubular body 20 includes the luer lock connection component 25 to which a fill material source may be coupled for transferring fill material 100, but any other effective mechanism for delivering fill material 100 to the tubular body 20 may be used.

Figure 6B:
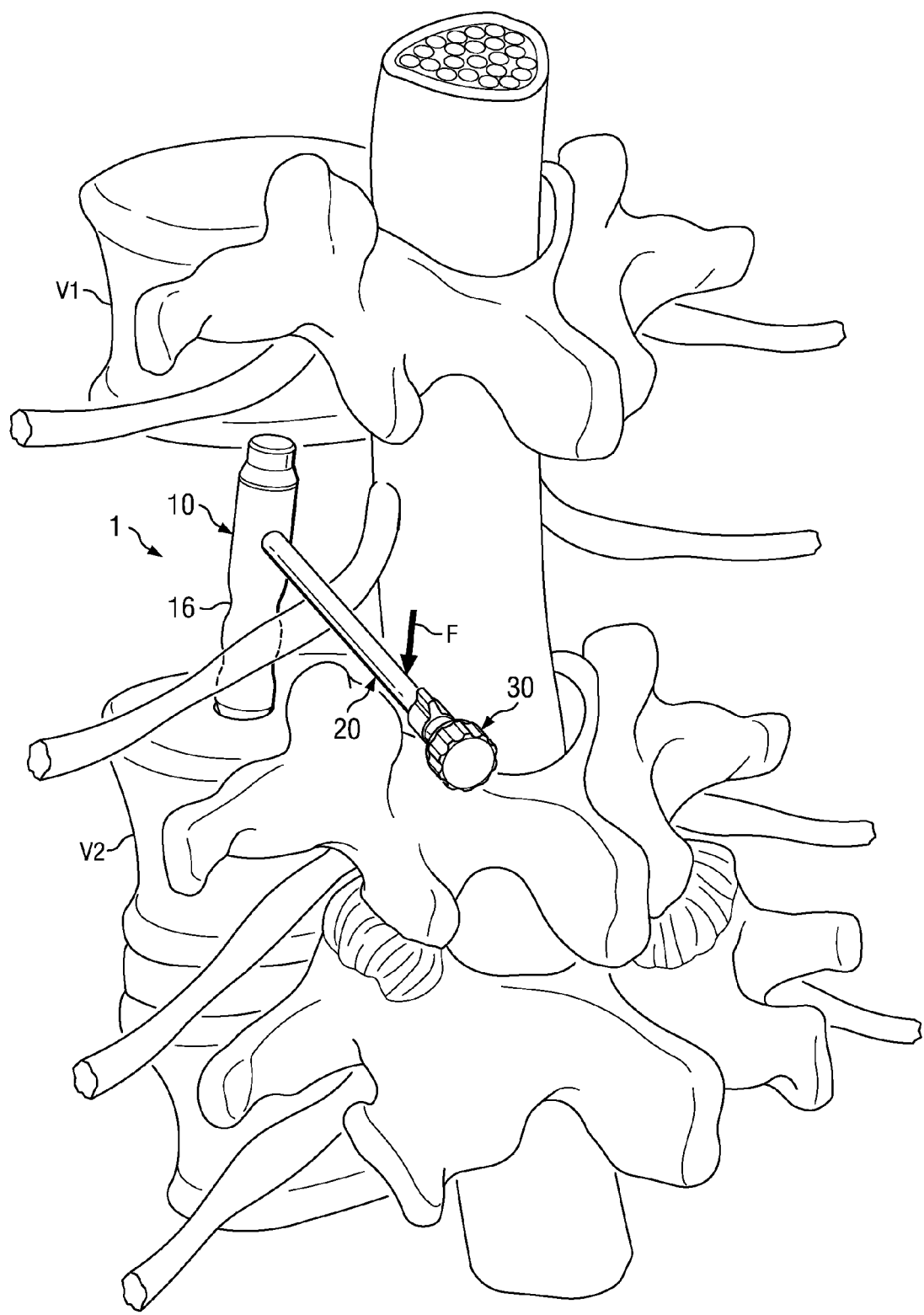
FIG. 6B is a perspective view of the embodiment of FIG. 1 being compressed as it is inserted between skeletal structures.
Figure 6C:
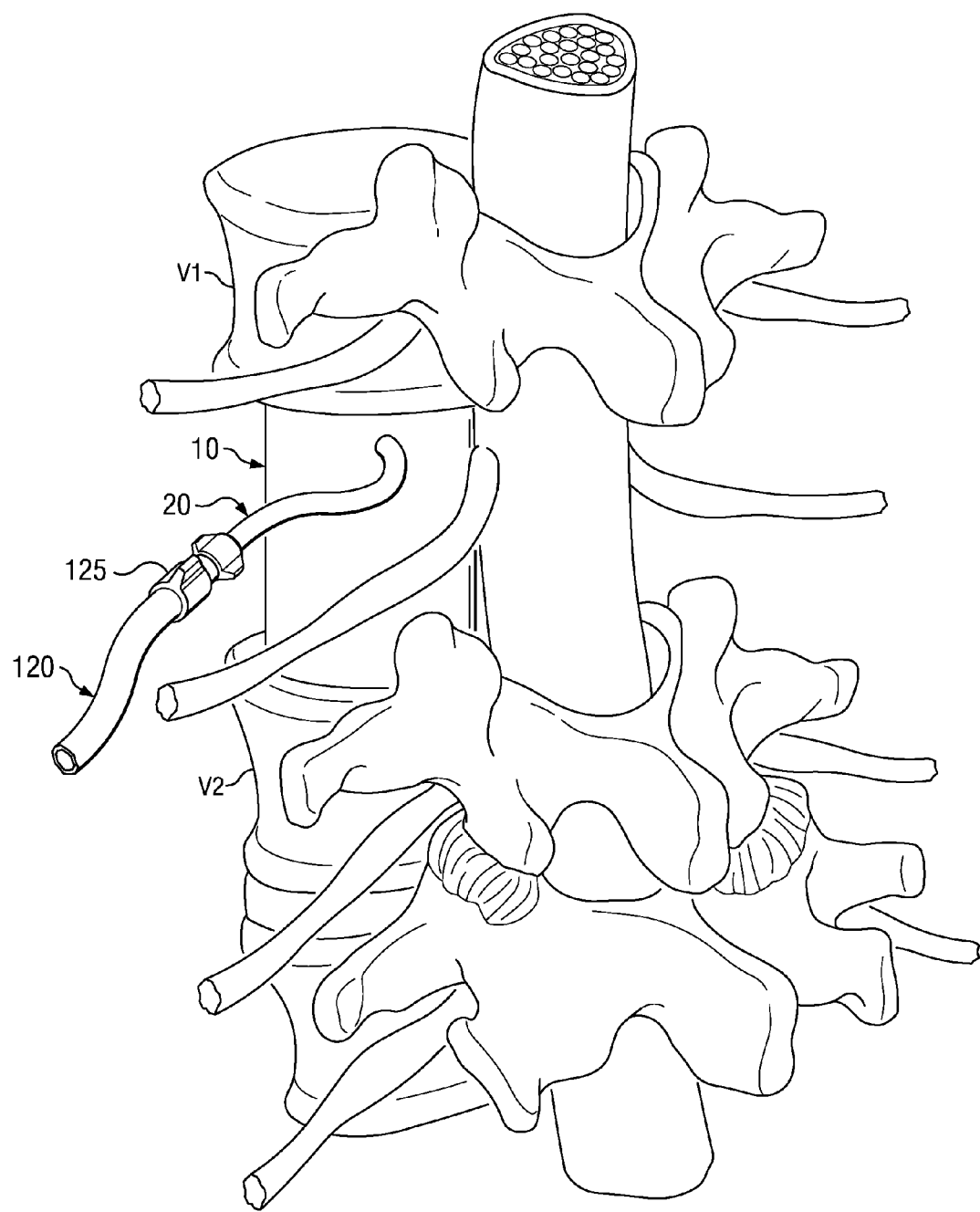
FIG. 6C is a perspective view of the embodiment of FIG. 1 in an at least partially expanded state and connected to a fill material source.

As shown in FIG. 6B, some method embodiments may include applying a force F to the tubular body 20 in a direction lateral to the longitudinal axis of the tubular body 20 to compress a first end of the expandable medical implant 10 to which the tubular body 20 is coupled toward a second end of the expandable medical implant 10 that is substantially opposite from the first end of the expandable medical implant 10. The force F illustrated is a pushing linear force to compress the expandable medical implant 10, but in other embodiments the force may be a pulling, twisting, combination force, or any effective force to compress a complementary medical implant. As illustrated in FIGS. 6A-6C collectively, the second end of the expandable medical implant 10 is placed against the second vertebra V2 to compress the expandable medical implant 10. Deformations 16 in the membrane 15 are illustrated in FIG. 6B, indicating compression in the expandable medical implant 10 and buckling of the membrane 15. The expandable medical implant 10 may be further compressed to cause the first end to clear the first vertebra V1. The expandable medical implant 10 may then be aligned with the first vertebra V1, as illustrated in FIG. 6C. This alignment may be carried out under direct vision, with the aid of optical instruments, in combination with radiographic equipment or surgical navigation equipment, or by any other effective mechanism. Embodiments of the reinforcing member 30 give the tubular body 20 adequate bending strength to transfer load of the force F to the expandable medical implant 10 to compress the expandable medical implant 10.

Method embodiments may also include cutting off a portion of a tubular body, such as the tubular body 20, that extend beyond the medical implant after the medical implant is a least partially filled with the fill material 100, or some other substance. Cutting of a tubular body may provide a safer final construct that is more compact and less likely to interfere with anatomical structures. For some fill materials, cutting of the tubular body 20 before the fill material sets entirely is advantageous when fill material remains in the tubular body 20. Additionally, the material from which a tubular body is made may contribute to or distract from the ability to cut the tubular body.

An embodiment of the invention is a method of stabilizing spaced apart skeletal structures. Method embodiments may be accomplished with a device including a medical implant configured to receive a fill material, such as the expandable medical implant 10, and a fill material source, such as the fill material sources disclosed herein and including a supply tube 120 with supply luer lock 125, as illustrated in FIG. 6C. The device may include a tubular body, such as the tubular body 20, having a distal end 21 and a proximal end 22 (FIG. 2). The tubular body 20 is shown coupled to the expandable medical implant 10 at the distal end 21 of the tubular body 20 and configured to provide a conduit between the fill material source and the expandable medical implant 10. The device may also include a reinforcing member, such as the reinforcing member 30, which is configured to at least supplement the bending strength of the tubular body 20. The reinforcing member 20 illustrated includes a distal end 39 that provides support along at least a portion of the tubular body and a proximal end 38 configured to couple over the proximal end 22 of the tubular body 20. In the illustrated embodiment, the proximal end 38 includes a knob 32 that couples over the proximal end 22 of the tubular body 20. In this embodiment, the full inside diameter of the opening of the tubular body 20 at the proximal end 22 is covered by the knob 32. In some embodiments, only a portion of the opening of the inside diameter or the tubular body 20 at the proximal end 22, or some other limited portion of the proximal end 22, may be covered.

Method embodiments as illustrated may include grasping the device by one or both of the tubular body 20 and the reinforcing member 30 and inserting the device between skeletal structures, such as the first vertebra V1 and the second vertebra V2 by manipulating the device by one or both of the tubular body 20 and the reinforcing member 30. In some embodiments, a reinforcing member, such as the reinforcing member 30, is a solid rod that is removed from the tubular body 20 prior to moving fill material 100 into the tubular body 20. An example of removing the reinforcing member 30 from the tubular body 20 is depicted in the exploded view of FIG. 2. The method embodiments shown also include transferring fill material from the fill material source, through the proximal end 22 of the tubular body, and into the expandable medical implant 10. A supply tube 120 with supply luer lock 125, as illustrated in FIG. 6C, is in place to transfer fill material to the tubular body 20 and medical implant 10. The medical implants 10 of FIGS. 5 and 6C are shown with at least a portion of fill material 100 transferred to them. In an embodiment where a reinforcing member is a cannulated rod, a fill material source may be connected to the cannulated rod prior to transferring fill material, rather than being required to remove the reinforcing member prior to transferring fill material.

The expandable medical implant is shown in FIGS. 6A-8 as being implanted from a generally posterior approach. However, embodiments of the invention may include implantation from any surgical approach, including but not limited to, lateral, anterior, transpedicular, lateral extracavitary, in conjunction with a laminectomy, in conjunction with a costotransversectomy, or by any combination of these and other approaches.

Various method embodiments of the invention are described herein with reference to particular devices. However, in some circumstances, each disclosed method embodiment may be applicable to each of the implants, or to some other implant operable as disclosed with regard to the various method embodiments.

Terms such as lower, upper, anterior, posterior, lateral, medial, and the like have been used herein to note relative positions. However, such terms are not limited to specific coordinate orientations, but are used to describe relative positions referencing particular embodiments. Such terms are not generally limiting to the scope of the claims made herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A system configured to stabilize spaced apart skeletal structures comprising:
   an expandable medical implant configured to receive a fill material;
   a tubular body having a distal end and a proximal end, the tubular body being coupled to the expandable medical implant at the distal end of the tubular body and configured to provide a conduit between a fill material source and the expandable medical implant, the tubular body being a flexible construct incapable of supporting a weight or insertion force of the expandable medical implant in a direction transverse to a longitudinal axis of the tubular body without deformation; and
   a reinforcing member disposed within an inside diameter of the tubular body configured to supplement the bending strength of the tubular body, the reinforcing member being a rigid construct capable of supporting the weight or insertion force of the expandable medical implant in the direction transverse to the longitudinal axis of the tubular body, wherein the reinforcing member includes a distal end that provides support along the tubular body between the expandable medical implant and the proximal end of the tubular body and a proximal end configured to securely couple over the proximal end of the tubular body.

2. The system of claim 1 wherein the expandable medical implant is a vertebral body replacement device.

3. The system of claim 1 wherein the reinforcing member is a rod.

4. The system of claim 1 wherein the reinforcing member is a tube.

5. The system of claim 1 wherein the reinforcing member is a solid rod.

6. The system of claim 1 wherein the reinforcing member is a cannulated rod.

7. The system of claim 1 wherein the reinforcing member includes threads near the proximal end of the reinforcing member configured to engage with at least a portion of the proximal end of the tubular body.

8. The system of claim 1 wherein the tubular body fully covers the proximal end of the reinforcing member.

9. The system of claim 1, further comprising a fill material configured to be passed through the tubular body and be received in the expandable medical implant.

10. The system of claim 1 wherein the reinforcing member has a length that is greater than a length of the tubular body such that the distal end of the reinforcing member extends through the distal end of the tubular body.

* * * * *